(12) United States Patent
Avirutnan et al.

(10) Patent No.: US 7,629,117 B2
(45) Date of Patent: Dec. 8, 2009

(54) DETERMINATION OF RISK OF DEVELOPING DENGUE HEMORRHAGIC FEVER/DENGUE SHOCK SYNDROME, METHODS AND COMPOSITIONS THEREFOR

(75) Inventors: Panisadee Avirutnan, Bangkok (TH); Prida Malasit, Bangkok (TH); Sucharit Bhakdi Punyaratabhandu, Mainz (DE); Watchara Kasinrerk, Chaing Mai (TH); Chunya Pauttikhunt, Bangkok (TH)

(73) Assignee: Mahidol University, Bangkok (TH)

( * ) Notice: Subject to any disclaimer, the term of this patent is extended or adjusted under 35 U.S.C. 154(b) by 0 days.

(21) Appl. No.: 11/764,019

(22) Filed: Jun. 15, 2007

(65) Prior Publication Data

US 2008/0113338 A1 May 15, 2008

Related U.S. Application Data

(60) Provisional application No. 60/815,136, filed on Jun. 20, 2006.

(51) Int. Cl.
*C12Q 1/70* (2006.01)
*G01N 33/53* (2006.01)
*A61K 39/42* (2006.01)
*A61K 39/12* (2006.01)

(52) U.S. Cl. .................. 435/5; 435/7.1; 424/159.1; 424/218.1

(58) Field of Classification Search .................. None
See application file for complete search history.

(56) References Cited

U.S. PATENT DOCUMENTS 6,870,032 B1 3/2005 Flamand

OTHER PUBLICATIONS

Avirutnan et al. The Journal of Immunology, 1998, 161:6338-6346.*
Avirutnan et al. The Journal of Infectious Diseases, 2006, 193:1078-1088.*
Libraty et al. The Journal of Infectious Diseases, 2002, 186:1165-1168.*
Lam et al. Clinical and Diagnostic Virology, 1998, 10:75-81.*
Alcon et al, Enzyme-linked immunosorbent assay specific to dengue virus type 1 nonstructural protein NS1 reveals circulation of the antigen in the blood during the acute phase of disease in patients experiencing primary or secondary infections, J Clin Microbiol, 2002, 40:376-81.
Avirutnan et al, Dengue virus infection of human endothelial cells leads to chemokine production, complement activation, and apoptosis, J Immunol, 1998, 161:6338-46.

Bhakdi and Kazatchkine, Pathogenesis of dengue: an alternative hypothesis, Southeast Asian J Trop Med Public Health, 1990, 21:652-7.
Bokisch et al, The potential pathogenic role of complement in dengue hemorrhagic shock syndrome, N Engl J Med, 1973, 289:996-1000.
Cardiff et al, Immunological and biophysical separation of dengue-2 antigens, J Virol, 1971, 7:15-23.
Dengue haemorrhagic fever: diagnosis, treatment, prevention and control, Geneva: World Health Organization, 1997.
Falconar and Young, Immunoaffinity purification of native dimer forms of the flavivirus non-structural glycoprotein, NS1, J Virol Methods, 1990, 30:323-32.
Falgout et al, Immunization of mice with recombinant vaccinia virus expressing authentic dengue virus nonstructural protein NS1 protects against lethal dengue virus encephalitis, J Virol, 1990, 64:4356-63.
Falkler et al, Human antibody to dengue soluble complement-fixing antigens, J Immunol, 1973, 111:1804-9.
Guzman et al, Epidemiologic studies on dengue in Santiago de Cuba, 1997, Am J Epidemiol, 2000, 152:793-9.
Halstead and O'Rourke, Dengue viruses and mononuclear phagocytes. 1. Infection enhancement by non-neutralizing antibody, J Exp Med, 1977, 146:201-7.
Halstead, Antibody, macrophages, dengue virus infection, shock, and hemorrhage: a pathogenic cascade, Rev Infect Dis, 1989, 11 suppl 4:S830-9.
Halstead, Pathogenesis of dengue: challenges to molecular biology, Science, 1988, 239:476-81.
Henchal et al, Synergistic interactions of anti-NS1 monoclonal antibodies protect passively immunized mice from lethal challenge with dengue 2 virus, J Gen Virol, 1988, 69:2101-7.
Huang et al, Antibody responses to an immunodominant nonstructural 1 synthetic peptide in patients with dengue fever and dengue hemorrhagic fever, J Med Virol, 1999, 57:1-8.
Kuno et al, Study of anti-dengue NS1 antibody by western blot, J Med Virol, 1990, 32:102-8.

(Continued)

*Primary Examiner*—Stacy B Chen
(74) *Attorney, Agent, or Firm*—Sonnenschein, Nath and Rosenthal LLP (57) ABSTRACT

The present specification discloses methods of determining risk of developing Dengue Hemorrhagic Fever/Dengue Shock Syndrome (DHF/DSS) in an individual infected with dengue virus (DV). The methods comprise determining, in a fluid or tissue sample of an individual, the presence, absence or quantity of dengue virus protein NS1, and determining, in a fluid or tissue sample of the individual, presence, absence or quantity of SC5b-9 complement complex. The methods can further comprise comparing the levels of NS1 protein and SC5b-9 complement complex with a database comprising epidemiological data correlating levels of NS1 protein and SC5b-9 complement complex with probability of developing DHF/DSS in a population.

9 Claims, 7 Drawing Sheets

OTHER PUBLICATIONS

Kurane et al, Immunopathologic mechanisms of dengue hemorrhagic fever and dengue shock syndrome, Arch Virol Suppl, 1994, 9:59-64.

Libraty et al, High circulating levels of the dengue virus nonstructural protein NS1 early in dengue illness correlate with the development of dengue hemorrhagic fever, J Infect Dis, 2002, 186:1165-8.

Malasit, Complement and dengue haemorrhagic fever/shock syndrome, Southeast Asian J Trop Med Public Health, 1987, 18:316-20.

Mongkolsapaya et al, Original antigenic sin and apoptosis in the pathogenesis of dengue hemorrhagic fever, Nat Med, 2003, 9:921-7.

Murgue et al, Prospective study of the duration and magnitude of viraemia in children hospitalized during the 1996-1997 dengue-2 outbreak in French Polynesia, J Med Virol, 2000, 60:432-8.

Nimmannitya, Clinical spectrum and management of dengue haemorrhagic fever, Southeast Asian J Trop Med Public Health, 1987, 18:392-7.

Pathogenic mechanisms in dengue hemorrhagic fever: report of an international collaborative study, Bulletin World Health Organization, 1973, 48:117-33.

Puttikhunt et al, Production of anti-dengue NS1 monoclonal antibodies by DNA immunization, J Virol Methods, 2003, 109:55-61.

Qu et al, Immunoreactivity and protective effects in mice of a recombinant dengue 2 Tonga virus NS1 protein produced in a baculovirus expression system, J Gen Virol, 1993, 74:89-97.

Russell et al, Immunoprecipitation analysis of soluble complement-fixing antigens of dengue viruses, J Immunol, 1970, 105:838-45.

Sangkawibha et al, Risk factors in dengue shock syndrome: a prospective epidemiologic study in Rayong, Thailand. 1. The 1980 outbreak, Am J Epidemiol, 1984, 120:653-69.

Schlesinger et al, Protection of mice against dengue 2 virus encephalitis by immunization with the dengue 2 virus non-structural glycoprotein NS1, J Gen Virol, 1987, 68:853-7.

Shu et al, Dengue NS1-specific antibody responses: isotype distribution and serotyping in patients with Dengue fever and Dengue hemorrhagic fever, J Med Virol, 2000, 62:224-32.

Vaughn et al, Dengue viremia tier, antibody response pattern, and virus serotype correlate with disease severity, J Infect Dis, 2000, 118:2-9.

Young et al, An antigen capture enzyme-linked immunosorbent assay reveals high levels of the dengue virus protein NS1 in the sera of infected patients, J Clin Microbiol, 2000, 38:1053-7.

* cited by examiner

DETERMINATION OF RISK OF DEVELOPING DENGUE HEMORRHAGIC FEVER/DENGUE SHOCK SYNDROME, METHODS AND COMPOSITIONS THEREFOR

CROSS-REFERENCE TO RELATED APPLICATIONS

This application claims the benefit of U.S. Provisional Application Ser. No. 60/815,136, filed Jun. 20, 2006, which is herein incorporated by reference in its entirety.

INTRODUCTION

The present Dengue disease is caused by infection with dengue virus (DV), an arthropod-borne virus transmitted by mosquitoes. Dengue virus is classified in the Flaviviridae family, genus *Flavivirus*. DV has been subdivided into 4 serotypes, DEN-1. DEN-2, DEN-3, and DEN-4.

Dengue virus is a single-stranded, positive-strand RNA virus with no DNA stage. Its genome has a length of approximately 11,000 nucleotide, and encodes a polyprotein of approximately 3400 amino acids. A newly synthesized polyprotein is processed and cleaved by cellular and viral proteases in the host cell to generate three structural proteins, including capsid (C), premembrane (PrM, precursor of the mature membrane protein, M), and envelope (E) proteins, and seven nonstructural (NS) proteins, NS1, NS2A, NS2B, NS3, NS4A, NS4B, and NS5.

Infection by DV can cause a variety of clinical syndromes ranging from asymptomatic, self-limiting febrile illness known as dengue fever (DF) to the severe vascular leakage syndrome, Dengue Hemorrhagic Fever/Dengue Shock Syndrome (DHF/DSS). Children at the age of 5-14 years old living in endemic regions are most susceptible to severe dengue disease although the virus can infect humans at any age. DHF/DSS is one of the major health problems of countries in tropical and subtropical regions of the world, causing over one hundred thousand hospitalizations and several thousand deaths annually worldwide.

After transmission of DV into a susceptible human by mosquito bite, it usually takes 3-8 days for an incubation period until clinical symptoms appear. An acute-biphasic fever is characteristic of DF, which can be accompanied by a variety of nonspecific signs and symptoms such as headache, backache, body-ache, nausea and vomiting, joint pains, weakness, and rash. Body temperature is usually in between 39° C. and 40° C., and the fever may be biphasic with the tendency to last for about 2 to about 7 days. Hemorrhagic manifestations in DF patients are common and range from mild to severe. Skin hemorrhages, including petechiae and purpura are the most common, along with gastrointestinal bleeding, gingival bleeding, epistaxis, and/or menorragia. Hematuria occurs infrequently. DF is generally self-limiting and is rarely fatal. The acute phase of illness lasts for up to about 7 days, but the convalescent phase can continue for weeks, and can also be associated with weakness and/or depression, especially in adults.

DHF is a severe form of DV-infection characterized by abnormalities in hemostasis and increased vascular permeability leading to plasma leakage and tendency toward bleeding. According to the World Health Organization (WHO), DHF is diagnosed in any DV-infected patients meeting the following criteria: acute sudden onset of high fever for 2-7 days, hemorrhagic manifestation with at least a positive tourniquet test, platelet count <$100 \times 10^9$/L, and hemoconcentration (rising packed cell volume >20%) or other evidence of plasma leakage such as ascites, pleural effusion, low level of serum protein/albumin. DHF is classified into 4 grades of increasing severity according to WHO criteria. DHF grade I is characterized by high grade fever, thrombocytopenia, hemoconcentration, positive tourniquet test and/or easy bruising. DHF grade II DHF is similar to DHF1, with additional spontaneous bleeding. DHF grade III, alternatively designated as DSS, is associated with massive vascular leakage leading to hypotension. The signs of shock includes rapid and weak pulse, narrow pulse pressure (20 mmHg or less), hypotension with cold, clammy skin and restlessness. DHF grade IV cases are those with profound shock with undetectable blood pressure or pulse. Uniquely, plasma leakage in DHF/DSS is caused by a selective increase in capillary permeability primarily at pleural and peritoneal spaces, resulting in pleural effusion and ascites. In some cases, serious bleeding with disseminated intravascular coaggulopathy (DIC) can complicate and worsen a patient's condition. Without proper. fluid supplementation and appropriate care, DSS patients rapidly deteriorate and death can result.

Typical cases of DHF/DSS initially present with symptoms including a sudden onset of high body temperature (>39° C.), which can accompany arthralgia, myalgia, headache, and/or vomiting. The critical stage is reached after 3-7 days of fever. Approximately 24 h before and 24 h after defervescence, signs of circulatory failure of varying severity can appear. Several symptoms and signs occur before defervescence which can serve as warnings of impending DSS. These symptoms and signs include generalized abdominal pain, persistent vomiting, change in level of consciousness, a sudden drop in platelet count, and a rapid rise in hematocrit. By this time, most patients also show evidence of pleural effusion on a chest radiograph. If plasma loss continues and becomes excessive, a patient can progress into profound shock. The outcome of DHF/DSS therefore depends on early diagnosis and immediate replacement of fluid.

Four Dengue virus serotypes exist, and DHF/DSS occurs almost exclusively in patients suffering from a secondary infection with a second virus serotype. Following re-infection, enigmatic dysfunction of the immune system can lead to enhanced viral replication. High levels of viremia and of circulating viral antigens are consequently found in patients following a secondary infection. (Vaughn, D. W. et al., J. Infect. Dis. 181: 2-9, 2000; Murge, B., et al., J. Med. Virol. 60: 432-438, 2000; Libraty, D. H., et al., J. Infect. Dis. 186: 1165-1168, 2002).

Nonstructural protein NS1 is a dengue complement-fixing antigen (P. K. Russel et al., J. Immuno., 105: 838-845, 1970; G. W. Smith et al., J. Gen Virol. 66: 559-571, 1985; Brandt et al., 1970; Cardiff et al., 1971). This glycoprotein is highly conserved in the *flavivirus* genus, in particular in the four dengue virus serotypes. The protein i not present on mature viral particles, accumulates on the plasma membrane of infected ceils and is also excreted from infected cells, primarily as a soluble hexameric oligomer (Falconar and Young, 1990; Flamand et al., 1999; Winkler et al., 1989).

High levels of anti-NS1 antibodies have been found in the circulation of dengue-infected patients during late-acute and convalescent phase (Falkler et al., 1973; Huang et al., 1999; Kuno et al., 1990; Shu et al., 2000). Soluble NS1 (sNS1) has also been detected in dengue patient sera (Young et al., 2000; Alcon et al., 2002; Libraty et al., 2002).

Diagnosis of dengue virus infection can be made by physical examination of the patient and routine clinical laboratory tests such as complete blood count (CBC). A positive tourniquet test has been considered to be a sensitive parameter for dengue diagnosis. More than 90% of cases can be correctly diagnosed for dengue infection by history, physical signs, and a positive tourniquet test. However, definitive diagnosis for dengue virus as a causative agent requires laboratory confirmation, especially in regions where other endemic infectious diseases mimic the syndromes caused by dengue infection.

Definitive diagnostic tests for dengue infection include isolation of viable virus and identification of viral RNA in serum or plasma. However, several factors, such as timing of specimen collection and availability of equipment limit routine application of these tests.

Serological techniques are also used for dengue diagnosis. Because timing of specimen collection is flexible and immunoglobulins are not easily degraded or inactivated by harsh treatment of specimens therefore, serological tests are commonly used in the field. The most commonly used serological techniques for the diagnosis of dengue infection are the hemagglutination inhibition (HI) test, which detects total anti-dengue antibodies by the ability of dengue antibody to inhibit dengue virus-mediated agglutination of erythrocytes from geese or trypsinized human O red blood cells, and the immunoglobulin M or G (IgM or IgG) capture enzyme linked immunosorbent assay (ELISA). HI test and IgG-captured ELISA usually require paired acute and convalescent phase serum samples collected a week or more apart for definitive diagnosis based on a fourfold rise in anti-dengue antibody. Results from both IgM and IgG capture ELISA can be used to differentiate between the cases of primary and secondary infection: in primary infection, the ratio of anti-dengue IgM to anti-dengue IgG is relatively high for at least a month following infection, but in secondary infection, a rapid increase of IgG antibody generally occurs following infection, and the ratio of anti-dengue IgM to anti-dengue IgG in a single acute specimen is low.

U.S. Pat. No. 6,870,032 describes a method for early detection of a flavivirus-induced infection including dengue infection by detecting NS1 protein by a capture enzyme linked immunosorbant assay (ELISA) technique employing at least two antibodies, i.e., a first capture antibody for capturing the NS1 and a second antibody for detecting the presence of NS1 in biological samples.

Terminal complement complex (SC5b-9) is a group of proteins in the terminal pathway of complement system. It is not always generated when the complement system is triggered due to a tightly-control led set of the complement regulatory proteins. Only strong or efficient complement activators can successfully cause SC5-9 liberation. In healthy individuals, very low or insignificant level of terminal complement complex can be detected.

Complement activation is known to be a key pathogenic mechanism in DV-infection. Accelerated complement consumption and marked reduction of plasma complement components are observed in DSS patients during shock. However, the cause of complement activation has remained unknown.

Available dengue diagnostic assays do not offer the possibility of detecting DV infection during an early clinical period, and there is no assay available for predicting risk of developing DHF/DSS in persons with dengue fever, or identifying individuals in initial stages of DHF/DSS who may later succumb to severe and life-threatening disease outcomes.

SUMMARY

The present inventors have developed methods of determining risk of developing Dengue Hemorrhagic Fever/Dengue Shock Syndrome in individuals infected with dengue virus. These methods involve measuring levels of both NS1 protein and terminal complement SC5b-9 complex in a biological fluid or tissue sample. In various configurations, the methods comprise determining, in a fluid or tissue sample of an individual, the presence, absence or quantity of dengue virus protein NS1, and determining, in a fluid or tissue sample of the individual, presence, absence or quantity of SC5b-9 complement complex. In various aspects, an individual is considered to be at risk of developing DHS/DSS if a) the amount of NS1 protein is at least about 90 ng/ml and b) the amount of SC5b-9 complement complex is at least about 200 ng/ml.

In various configurations, determining presence, absence or quantity of dengue virus protein NS1 can comprise a) contacting a fluid or tissue sample from an individual with a solid surface comprising a first probe which specifically binds NS1 protein, wherein a complex forms comprising the probe and the NS1 protein, if present in the sample, b) contacting the solid surface with a second probe which specifically binds NS1 protein; and c) determining quantity of the second probe bound to the surface.

In various configurations, determining presence, absence or quantity of SC5b-9 complement complex can comprise a) contacting a fluid or tissue sample from an individual with a solid surface comprising a first probe which specifically binds SC5b-9 complement complex, wherein a complex forms comprising the probe and the SC5b-9 complement complex, if present in the sample, b) contacting the solid surface with a second probe which specifically binds SC5b-9 complement complex; and c) determining quantity of the second probe bound to the surface.

In various embodiments, the methods further comprise comparing the quantities of NS1 protein and SC5b-9 complement complex to data comprised by a database such as an epidemiological database comprising statistical correlations between NS1 protein and SC5b-9 complement complex quantities and probabilities of developing DHF/DSS. In various configurations, a health care provider such as a medical doctor can make a decision on whether to treat the individual, and which modalities of treatment to use, on the basis of the subject individual's profile of NS1 protein and SC5b-9 complement complex.

In various aspects, a fluid or tissue sample from an individual can be a body fluid sample such as a blood sample, a serum sample, a plasma sample, a lymphatic fluid sample or a cerebrospinal fluid sample.

In various configurations, types of probes which can be used in the present methods include, without limitation, antibodies, aptamers, kinases, avimers and combinations thereof. Antibodies can be monoclonal antibodies, polygonal antibodies or combinations thereof, and aptamers can be RNA aptamers, DNA aptamers, peptide aptamers, or combinations thereof.

A solid surface which can comprise a probe can be, without limitation, an ELISA plate, a bead, a dip stick, a test strip or a microarray.

In various aspects, binding of a second probe to a solid surface can be detected using any type of label known to skilled artisans, such as, for example, a fluorophore such as fluorescein, rhodamine, Cy3 or an ALEXA dye of Molecular Probes™ (Invitrogen), a hapten such as biotin or digoxygenin, an enzyme such as horseradish peroxidase, alkaline phosphatase, chloramphenicol acetyltransferase or luciferase, or a radioisotope such as $^{3}$H, $^{14}$C, $^{32}$P, or $^{35}$S. In various configurations, a hapten label can be detected by a secondary probe well known to skilled artisans, such as, for example, an enzyme-conjugated antibody directed against biotin or digoxygenin, or an enzyme-conjugated avidin or streptavidin. In addition, binding of a second probe to a solid surface can be quantified using any methods and devices known to skilled artisans, such as, without limitation, measuring fluorescence of a fluorophore linked to a second probe using a fluorimeter, or measuring light absorbance of a chromophore generated by hydrolysis of a chromogenic substrate of an enzyme linked to a secondary probe.

In various embodiments, linkage of a label to a second probe can be direct (for example, an enzyme such as horseradish peroxidase covalently attached to an antibody directed against NS1 protein or SC5b-9 complement complex) or indirect (for example, an enzyme covalently attached to goat anti-mouse serum, when the second probe is a mouse monoclonal antibody directed against NS1 protein or SC5b-9 complement complex, and when the first probe is not a mouse antibody).

In various embodiments, the inventors disclose kits which comprise components which can be used to assess individual risk of developing DHF/DSS. A kit of these embodiments comprises a first probe which specifically binds dengue virus protein NS1; a second probe which specifically binds dengue virus protein NS1; a first probe which specifically binds SC5b-9 complement complex; and a second probe which specifically binds SC5b-9 complement complex. In various aspects of a kit of these embodiments, each probe can be independently selected from the group consisting of an antibody, an aptamer, a kinase, an avimer and a combination thereof. In some aspects, each probe can be an antibody independently selected from the group consisting of a polyclonal antibody and a monoclonal antibody. In some aspects, a second probe comprised by a kit can further comprise a label. However, in some aspects, if a first antibody and a second antibody are directed against the same antigen and the antibodies derive from the same species, the second antibody requires a label which allows it to be detected and quantified independent of detection of the first antibody. Such a label can be, for example, a fluorophore, a hapten such as biotin or digoxygenin, or an enzyme. In addition, a second probe comprised by a kit can comprise a label, which can be, without limitation, a chromophore, a fluorophore, a hapten or an enzyme. An enzyme comprised by a second probe can be, without limitation, horseradish peroxidase, alkaline phosphatase, chloramphenicol acetyltransferase or luciferase. In various embodiments, a kit can further comprise a substrate for the enzyme.

BRIEF DESCRIPTION OF THE DRAWINGS

FIG. 2 illustrates complement activation by supernatants of dengue virus (DV)-infected cells. A, Dose dependency of spontaneous complement activation. The given amounts of culture supernatants were mixed with 25 μL of normal human serum (NHS), and buffer was added to give a total of 200 μL/sample. CH50 was determined after incubation at 37° C. for 1 h. Data are displayed as the mean±SD of the percentage CH50 over serum controls from 3 independent experiments. Final concentrations of NS1 in the samples are given on the second Y-axis. B, Enhancement of complement activation by DV-specific antibodies. Culture supernatants (100 μL) from DV-infected cells were mixed with purified antibodies from pooled convalescent-phase serum (PCS) and DV antibody-negative serum (DNS) at the given final concentrations and 25 mL of NHS. CH50 was determined after 60 min at 37° C. Data are displayed as the mean±SD of percentage CH50 over serum controls from 3 independent experiments. "0" indicates that the value of CH50 in the DV experiment was not detectable.

FIG. 3 illustrates activation of complement to completion by purified dengue virus (DV) NS1 protein. A, Purified soluble NS1 from DV-infected cells (iNS1s) at the given final concentrations was incubated in 12.5% normal human serum in the presence or absence of NS1-specific monoclonal antibody 2G6 (10 μg/mL) or pooled convalescent-phase serum (PCS) (20 μg/mL) at 37° C. for 1 h, and the SC5b-9 level was measured. B, Purified soluble NS1 from NS1 stably expressing cells (rNS1s) at the given final concentrations, tested for complement activation, as described in panel A. Equivalent concentrations of isotype control antibody and DV antibody-negative serum (DNS) were used as controls. EDTA (10 mmol/L) was added to inhibit complement activation for negative controls. Data are displayed as the mean±SD from 3 independent experiments.

FIG. 4 illustrates activation of complement to completion by membrane-associated NS1 (NS1m) in the presence of NS1-specific antibodies. A. Surface expression of dengue virus (DV) NS1 on DV-infected cells and on cells stably expressing NS1. Cells were stained with NS1-specific monoclonal antibody (MAb) 1A4, followed by fluorescein isothiocyanate (FITC)-conjugated anti-mouse immunoglobulin. Histogram plots were determined from data acquired from 5000 events in viable cells. The representative set of histograms is derived from 1 of 3 independent experiments. B and C, Colocalization of NS1 and complement C3 fragments on the surfaces of complement-attacked cells. DV-infected cells or cells expressing NS1m were incubated with 12.5% normal human serum (NHS) in the presence of a mix of purified NS1-specific MAbs. After 1 h at 37° C., cells were stained with fluorescent-conjugated secondary antibodies and observed by confocal microscopy. NS1 (Cy3; red) and complement (FITC; green) colocalized on the membranes. D, Formation of C5b-9 on cells. Mock or DV-infected cells were incubated with purified antibodies from pooled convalescent-phase serum (PCS) and DV antibody-negative serum (DNS) in the presence of 12.5% NHS. The deposition of membrane attack complexes was detected by flow cytometry after staining with a MAb against C5b-9 and FITC-conjugated secondary antibodies. Analysis was performed on 5000 viable cells. Data are displayed as the mean±SD from 3 independent experiments.

DETAILED DESCRIPTION

The present inventors describe herein methods for determining the risk of developing Dengue Hemorrhagic Fever/Dengue Shock Syndrome in an individual infected with, or believed to be infected with, dengue virus, such as a person exhibiting signs and symptoms of dengue fever. The methods comprise obtaining at least one body fluid or tissue sample from an individual, and quantifying both NS1 protein and terminal complement SC5b-9 complex content of the sample. A body fluid can be, for example, blood, serum, plasma, lymphatic fluid, or cerebrospinal fluid. In various embodiments, the methods can be used, for example, to identify those individuals in a population who are in greatest need of medical treatment to prevent emergence of severs DHS/DSS.

As used herein, "risk" refers to the probability of developing Dengue Hemorrhagic Fever and Dengue Shock Syndrome. In various aspects, the risk of an individual developing DHF/DSS can be determined by a) measuring NS1 protein and SC5b-9 complex levels for the individual and b) comparing the measured levels to levels reported in one or more databases comprising epidemiological statistics correlating NS1 protein levels, terminal complement SC5b-9 complex levels and probability of developing DHF/DSS. In some embodiments, a database can be comprised by a computer readable medium such as a compact disc, or the database can be comprised by text printed on paper. In some configuration, levels of NS1 protein and complement SC5b-9 complex, and correlations with probabilities of developing DHF/DSS can be those set forth as follows, based upon analysis of a patient population:

If we consider different cut point levels of the NS1, only picking data from Day −1 Working backwards (excluding those on day 0, 1, 2 and other convalescent data), we see that the lower level we use, the more patients with "other febrile illness" (OFI) will be included:

If NS1 is 125 ng/ml, no OFI patients will be included. If NS1 is 100 ng/ml, 1 out of 21 of the OFI patients will be included. If NS1 is 90 ng/ml, 8 out of 19 OFI patients will be included.

When we use different SC5B-9 complex levels to look at sensitivity and specificity of DHF vs. DF, we have the following conclusions:

Using data from day −1-backward specimens only:

1. If NS1 at 90 ng/ml is used as the cut point:
   At SC5B-9 complex at 200 ng, 79% of all the patients will be NS1+/− and SC5B-9 complex$^+$; about 70% DHF will be diagnosed with NS1+/− and SC5B-9 complex$^+$, 30% will be diagnosed with DF.
   At SC5B-9 complex at 250 ng, 60% of all the patients will be NS1+/− and SC5B-9 complex$^+$; about 83% DHF will be diagnosed with NS1+/− and SC5B-9 complex$^+$, 17% will be diagnosed with DF.
   At SC5B-9 complex at 300 ng, 41% of all the patients will be NS1+/− and SC5B-9 complex$^+$; about 87% DHF will be diagnosed with NS1+/− and SC5B-9 complex$^+$, 13% will be diagnosed with DF.

The higher SC5B-9 complex, more patients will be taken as SC5B-9 complex$^-$ with only NS1$^+$.

Less than 1% will have NS1$^-$ and SC5B-9 complex$^-$.

2. If NS1 at 100 ng/ml is used as the cut point:
   At SC5B-9 complex at 200 ng, 80% of all the patients will be NS1+/− and SC5B-9 complex$^+$; about 76% DHF will be diagnosed with NS1+/− and SC5B-9 complex$^+$.
   At SC5B-9 complex at 250 ng, 59% of all the patients will be NS1+/− and SC5B-9 complex$^+$; about 83% DHF will be diagnosed with NS1+/− and SC5B-9 complex$^+$.
   At SC5B-9 complex at 300 ng, 48% of all the patients will be NS1+/− and SC5B-9 complex$^+$; about 87.5% DHF will be diagnosed with NS1+/− and SC5B-9 complex$^+$;
   About 6% will be NS1$^-$ and SC5B-9 complex$^+$.

3. If NS1 at 125 ng/ml is used as the cut point:
   At SC5B-9 complex at 200 ng, 78% of all the patients will be NS1+/− and SC5B-9 complex$^+$; about 77.2% DHF will be diagnosed with NS1+/− and SC5B-9 complex$^+$.
   At SC5B-9 complex at 250 ng, 59% of all the patients will be NS1+/− and SC5B-9 complex$^+$; about 82.9% DHF will be diagnosed with NS1+/− and SC5B-9 complex$^+$.
   At SC5B-9 complex at 300 ng, 46% of all the patients will be NS1+/− and SC5B-9 complex$^+$; about 87.5% DHF will be diagnosed with NS1+/− and SC5B-9 complex$^+$;
   About 15% will be NS1 and SC5B-9 complex$^+$.

EXAMPLES

The following examples are provided for illustrative purposes only and are not to be construed as limiting the invention's scope in any manner. The description of an article, a composition, or a method in an example does not imply that the described article or composition has, or has not, been produced, or that that the described method has, or has not, been performed, regardless of verb tense. The methods and compositions described throughout this specification utilize laboratory techniques well known to skilled artisans and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; and Harlow, E., Using Antibodies: A Laboratory Manual, Cold Spring Harbor Laboratory Press, Cold Spring Harbor, N.Y., 1999.

Patients, materials and methods used in the present Examples include the following:

Patient enrollment and study design. A total of 182 patients admitted to the ward of Khon Khan Provincial Hospital, Thailand, between November 2001 and December 2003 who met the following 2 sets of criteria were enrolled in this prospective study. The first set of criteria included (1) age 1-15 years; (2) pyrexia for not more than 4 days, with no obvious source of infection; and (3) tourniquet test positivity or history of signs/symptoms of bleeding hemorrhagic diathesis. These patients subsequently all tested positive for DV by reverse-transcription polymerase chain reaction (RT-PCR), virus isolation, and DV antibody ELISA profiling. The second set of criteria included (1) age 1-15 years and (2) less than 3 days of fever with no obvious source of infection. Patients who subsequently tested positive for DV were included in the dengue fever (DF) and DHF groups, whereas those with negative RT-PCR and DV antibody results were assigned to the control "other febrile illness" (OFI) group. Blood specimens were collected daily in 5 mmol/L EDTA until 1 day after defervescence, and plasma samples were stored at −70° C. DV infection was confirmed by measuring anti-DV IgM/IgG and by RT-PCR [32]. Pleural fluid was aspirated only in patients experiencing severe respiratory difficulty, as a part of therapeutic measures to alleviate the pulmonary insufficiency caused by rapidly accumulated fluid.

Grading of DHF followed World Health Organization criteria [33]: DHF3 is assigned to patients with signs of circulatory failure, DHF2 is assigned to patients with spontaneous bleeding, and DHF1 is assigned to patients with fever who are tourniquet-test positive. Study day 0 was defined as the calendar day during which the patient's temperature fell and stayed below 37.8° C. The study protocol was approved by the Ministry of Public Health (approval date, 7 May 2003), the Faculty of Medicine Siriraj Hospital (certificates of approval 156/2002 and 115/2004), and the Khon Khan Hospital (approval date, 31 Oct. 2002). Informed consent was individually obtained from all subjects.

Reagents. IgG from pooled convalescent-phase serum (PCS) samples (hemagglutination titer, $\geq 1/25600$) and control serum samples (DV antibody-negative serum [DNS]) were purified by protein G column chromatography (Pharmacia). NS1-specific monoclonal antibody (MAb) clones 2G6, 1A4, 1B2, 1F11, 2E11, and 2E3 have been described elsewhere [29].

Cells and viruses. The swine fibroblast cell line (PsCloneD) and the insect cell line C6/36 were cultured at 37° C. and 28° C., respectively, in L-15 medium (Life Technologies) containing 10% tryptose phosphate broth (Sigma) and 10% fetal bovine serum (FBS) (Hyclone). The human kidney epithelial cell line HEK-293T was grown in RPMI 1640 (GIBCO) containing 10% FBS, 100 U/mL penicillin, and 100 µg/ml, streptomycin. DV serotype 1 (DEN-1), DEN-2, DEN-3, and DEN-4 (strain Hawaii, 16681, H-87, and H-241, respectively) were propagated in C6/36 cells [17].

Two HEK-293T cell lines expressing NS1 were conventionally generated [30]. Cells were transfected with pcDNA3.1/Hygro (Invitrogen) containing the coding sequence of NS1s (the complete sequence of NS1) or NS1m (the complete NS1 sequence connected to the 26-aa region at the N-terminus of NS2A).

NS1 purification. Fibroblast monolayers were infected with DEN-1, -2, -3, and -4 at an MOI of 1 and were cultured in protein-free medium (Ultradoma). Culture supernatants were harvested 3 days later, centrifuged at 200,000 g, and subjected to immunoaffinity chromatography with a column prepared with anti-NSI MAb 2G6.

For isolation of NS1s from transfected cells, culture supernatants were harvested every 3 days and replaced with fresh medium. Supernatants were passed through a 0.2-µm filter before immunoaffinity chromatography. Purified NS1 was passed over a protein G column twice to remove any traces of contaminating antibodies.

NS1 ELISA. Microtiter plates (Nunc) were coated with MAb 2E11 (5 µg/mL) overnight at 4° C. After blocking with PBS containing 15% FBS, wells were washed 5 times with PBS/0.05% Tween-20. Samples (100 µL) were added to each well and incubated for 1 h at room temperature. After 5 washes, 100 µL of MAb 2E3 (50 µg/mL) was added to each well and incubated for 1 h. The ELISA was developed conventionally, using horseradish peroxidase-conjugated goat anti-mouse IgG (Sigma).

Assay for fluid-phase complement activation. Cell supernatants or purified NS1s from DV-2 were incubated with 12.5% normal human serum (NHS) (final concentration) in a 0.2 mL, total assay volume in the presence or absence of anti-DV antibodies for 60 min at 37° C. Heat-inactivated serum or serum containing 10 mmol/L EDTA served as a negative control. Hemolytic complement titers (CH50) were determined in the conventional manner. SC5b-9 measurements were performed using a commercial ELISA from Quidel.

Assay for complement activation on cells. HEK-293T cells were infected with DV-2 at an MOI of 10 and were harvested 24 h after infection. DV-infected cells or cells expressing NS1 m ($1\times10^6$) were incubated with purified PCS, DNS, a mix of anti-NS1 MAbs, or isotype controls, in the presence of 12.5% NHS. Washed cells were incubated with a MAb against C3dg, provided by P. J. Lachmann, or against SC5b-9 complexes (Quidel); this was followed by staining with fluorescein isothiocyanate (FITC)-labeled rabbit F(ab')$_2$ anti-mouse immunoglobulin. Double staining for C3 and NS1 was performed by first reacting cells with a mix of anti-NS1 MAbs at 37° C. for 1 h. After 1 wish, cells were fixed with 2% paraformaldehyde for 10 min and incubated with rabbit anti-human C3c and C3d (Dakopatts). Stainings were developed with FITC-conjugated swine anti-rabbit immunoglobulins (Dako) and Cy3-conjugated goat anti-mouse immungloubulins (Jackson Immuno Research Laboratories). Washed cells were resuspended in 50% fluorescent mounting medium (Dako) and observed under a Zeiss LSM 510 META confocal microscope (Carl Zeiss).

Quantitative RT-PCR. RNA was extracted from DV-infected cell supernatants or patients' plasma by use of QIAamp Viral RNA Mini Kit (Qiagen), aliquoted, and stored at −70° C. Viral RNA was quantified by a single-tube 1-step real-time RT-PCR using a LightCycler instrument and software version 3.5 (Roche Molecular Biochemicals), as described by Shu et al. [31].

Measurement of anaphylatoxins. C3a and C5a were quantified using a commercial cytometric bead array kit (Becton Dickinson).

Statistical analysis. Data analysis was performed using SAS (version 8.1 SAS Institute). Viral load, NS1 level, and SC5b-9 level are presented as mean and SD and, in cases of skewness, as median and range. The $\chi^2$ test and 1-way analysis of variance were used to compare differences in sex and age, respectively, between groups of patients.

Since viral load, NS1 level, and SC5b-9 level were repeatedly observed over time and there were some missing data, a mixed model (MixMod) was employed as a multivariate statistical method. The purpose was to test the differences in patterns of viral load, NS1 level, and SC5b-9 level over time between different groups of patients. Under a random intercept model, mixed models with day (−3, −2, −1, 0, 1 and 2) as a quantitative variable were fitted. Only patients with data on at least 3 consecutive days were included in the analysis. Since viral load, NS1, and SC5b-9 were positively skewed, a common log transformation was applied. Residual analysis was performed to assure that model assumptions were satisfied. All analyzed P values were 2-sided.

Study participants. The overall male-to-female ratio among the 182 patients was 1:1, and the mean±SD age was 9.6±3 years (range, 2-15 years; median, 9 years). There were no major differences in sex ratios and mean ages of patients in each group. There were 49 patients with DF, 44 with DHF1, 44 with DHF2, 26 with DHF3/DSS, and 19 with OFIs. DV RTPCR results were positive for 151 (92.6%) of 163 patients infected with DV. The virus types identified were DEN-1 (n=87), DEN-2 (n=52), DEN-3 (n=6), and DEN-4 (n=6). Secondary infection was diagnosed in 148 patients (90.8%), and primary infection was diagnosed in 15 patients (9.2%). Of the primary infection cases, 67% were classified as DF (n=10), and the rest were classified as DHF1 (n=2), DHF2 (n=2), or DHF3 (n=1).

Example 1

Figure 1:
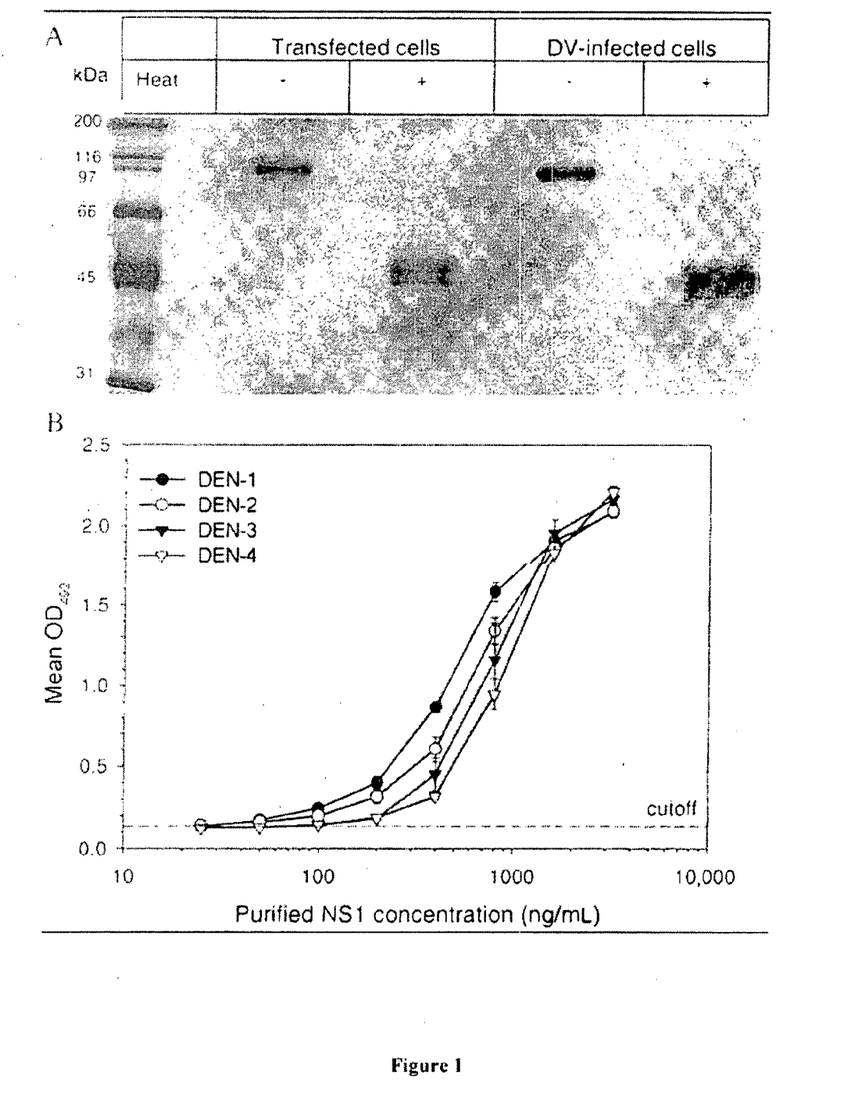
FIG. 1 illustrates presence of NS1 in Dengue-infected cells and NS1 capture ELISA. A, SDS-PAGE of purified soluble NS1 from dengue virus (DV)-infected cells and from cells stably expressing NS1. Purified NS1 was unheated or heated (at 95° C. for 3 min) before SDS-PAGE. Molecular weight markers (kDa) are shown in the far left column. B, standard curves for NS1 capture ELISA with purified NS1 from DEN-1, -2, -3, and -4. Data points represent the mean and SD for 3 replicates. The cutoff value was set at twice the mean optical density value for negative control samples (mean±SD, 0.103±0.025).

Purification of NS1s. FIG. 1A depicts SDS-PAGE of purified NS1. As described by Winkler et al. [18], the 80-kDa dimeric form was converted to the 40-kDa monomer by heating. The same bands appeared in Western blots with NS1-specific MAbs (data not shown). The mean±SD NS1 level in 3-day supernatants of infected cells ranged from 900.3±46.7 to 1029.4±62.4 ng/mL, and the yield of NS1 was 334±87.5 and 237.4±38.5 µg/L of culture from DV-infected cells and from NS1-transfected cells, respectively.

Example 2

NS1 capture ELISA. Antibodies employed in the capture ELISA cross-reacted with NS1 from all 4 DV serotypes. The detection limit for NS1 was found to be ~50 ng/mL from DV-1 and DV-2, 120 ng/mL for DV-3, and 160 ng/mL for DV-4 (FIG. 1B).

Example 3

Figure 2:
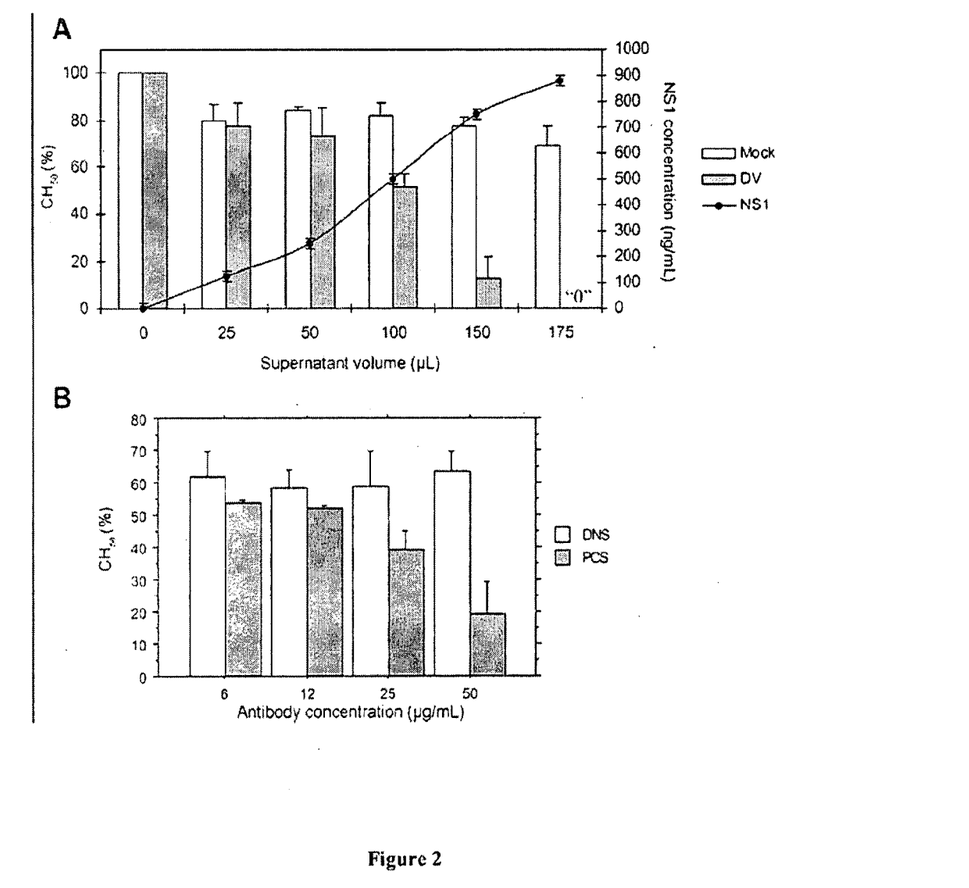

Activation of complement by NS1s. Supernatants from DV-infected cells, but not from mock-infected cells, dose dependently consumed complement in pooled human serum (FIG. 2A). Addition of purified immunoglobulin fractions from PCS but not control DNS enhanced complement consumption (FIG. 2B). An increase in complement activation was also observed when a mix of MAbs against NS1 was employed (data not shown).

Figure 3:
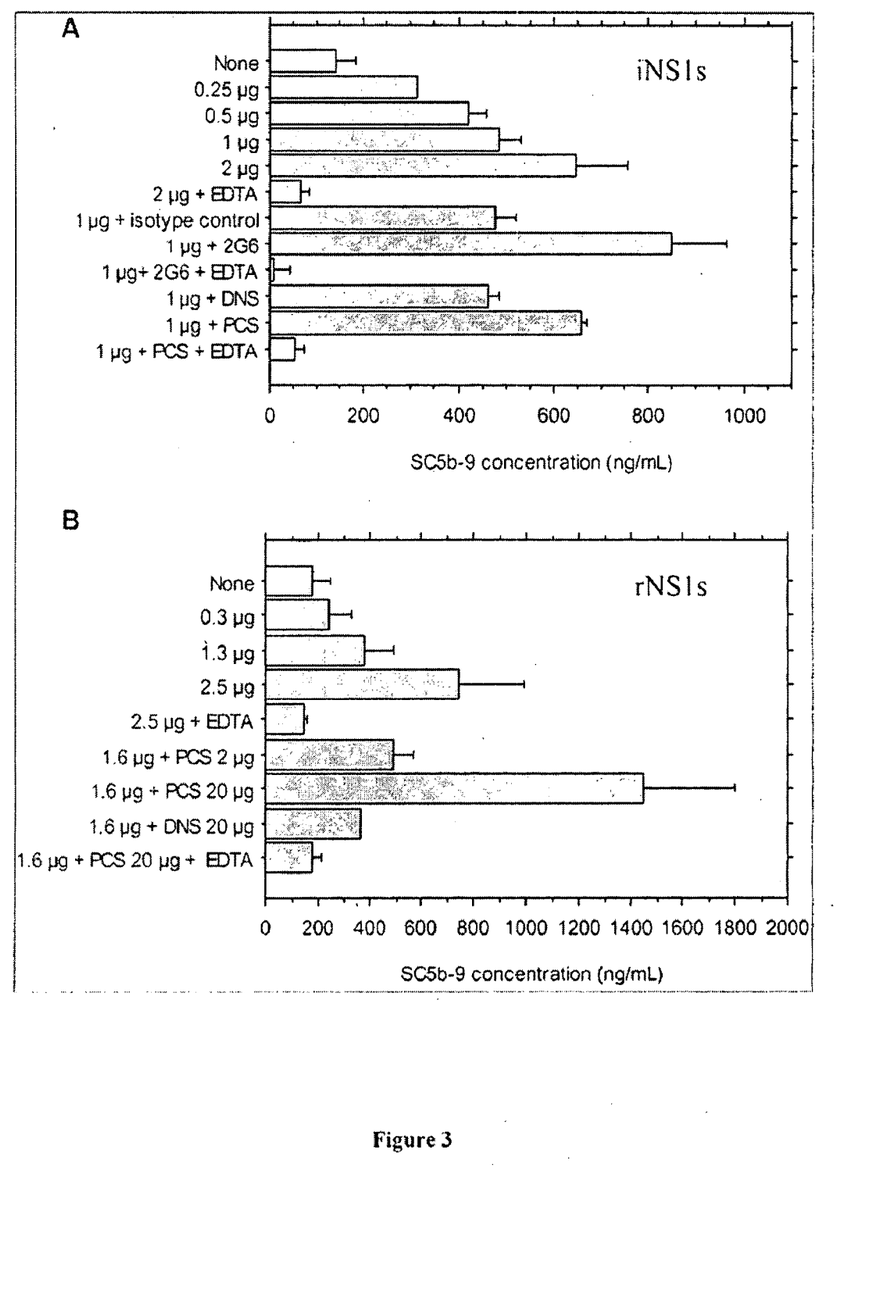

NS1s purified from supernatants of infected cells also activated complement and caused a decrease in CH50 similar to that caused by the unfractionated culture supernatants. Complement activation occurred to completion with formation of SC5b-9 (FIG. 3A) and was enhanced by NS1-specific MAbs and by purified immunoglobulin fractions from PCS but not by isotype-control antibodies or by purified immunoglobulin from DNS (FIG. 3A). Similar results were obtained with purified recombinant NS1s from transfected cells (FIG. 3B). Fractions from the protein G columns containing little or no NS1 had no complement-consuming activity.

Example 4

Figure 4:
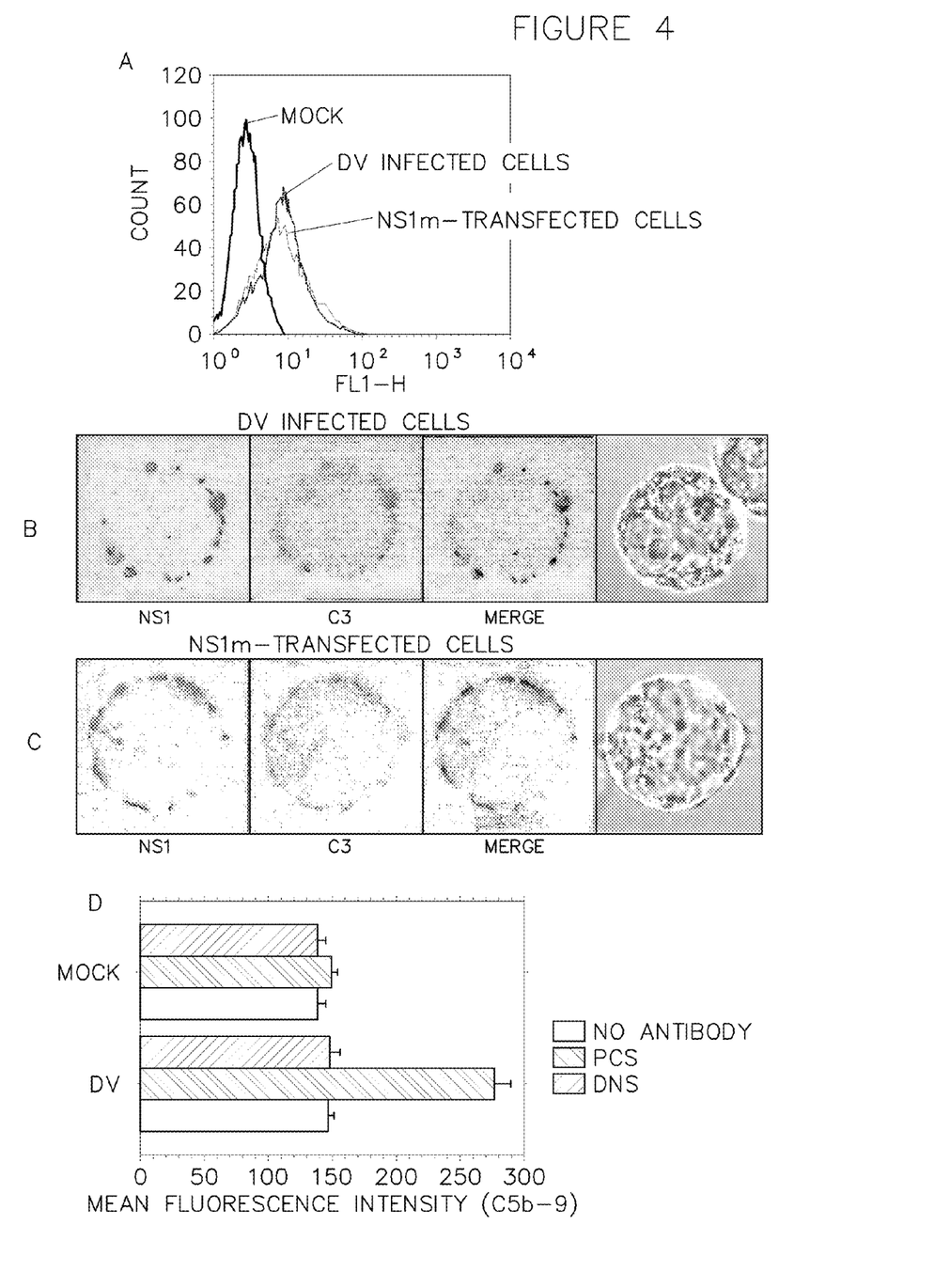

Antibody dependency of complement activation by cell-associated NS1. NS1 was expressed on the surface of DV-infected cells and on NS1m-transfected cells (FIG. 4A). When DV-infected cells were incubated with 12.5% NHS, no complement activation was observed, as was evident from negative staining for C3dg (data not shown) and C5b-9 (FIG. 4D) on cell surfaces. However, the presence of purified antibodies against NS1 triggered complement activation, as evidenced by colocalization of complement C3 and NS1 on the cells (FIG. 4B). Similar results were obtained with purified immunoglobulin from PCS (data not shown). Antibody-dependent complement activation was induced by all 4 clones of NS1-specific MAbs tested but not by isotype control antibodies. Colocalization of NS1 and C3dg was also observed after antibody-dependent complement activation on NS1m-transfected cells (FIG. 4C). Parallel immunoflouorescent staining for C5b-9 revealed its deposition oh the plasma membrane of DV-infected (FIG. 4D) and transfected (data not shown) cells.

Example 5

Figure 5:
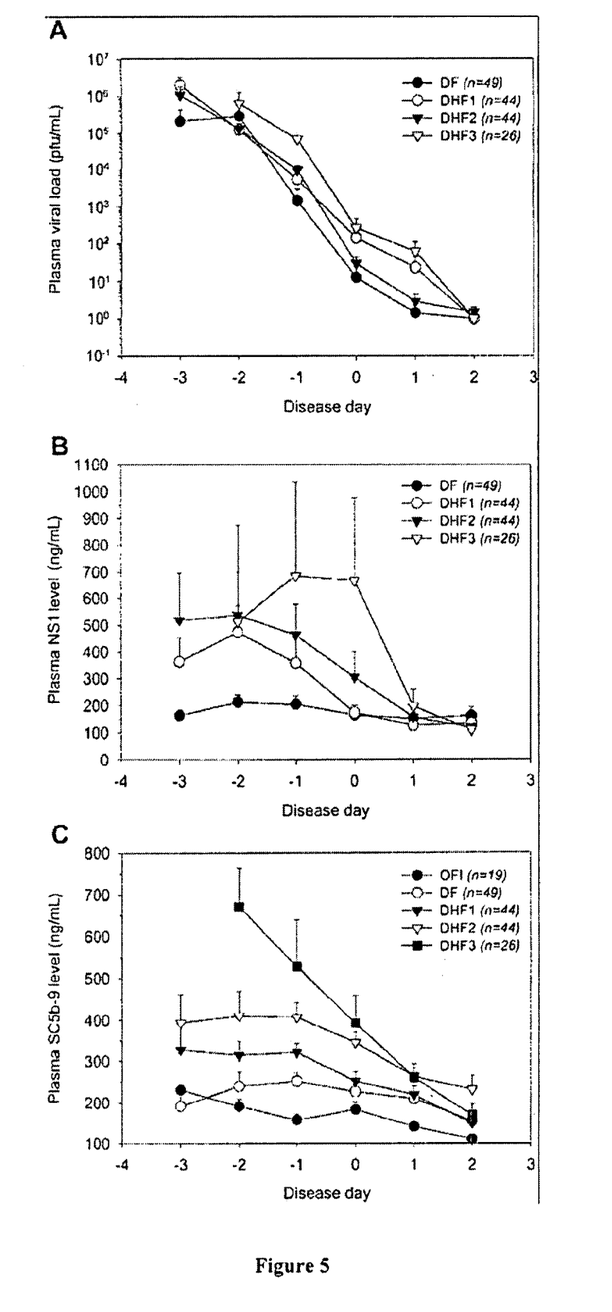
FIG. 5 illustrates viral loads, NS1 protein levels, and terminal SC5b-9 complexes in the circulation of patients with dengue fever (DF) and dengue hemorrhagic fever (DHF) and dengue shock syndrome. Plasma samples were assayed for dengue virus (DV) RNA levels by use of quantitative real-time reverse transcription polymerase chain reaction, and soluble NS1 and SC5b-9 complexes were quantified by ELISA. Disease day 0 was defined as the calendar day during which the temperature fell and stayed below 37.8° C. Plasma samples from patients with acute febrile diseases other than dengue (other febrile illnesses [OFIs]) were also used as controls. Plots show the mean and SE. NS1 levels were not detectable in patients with OFIs.
Figure 6:
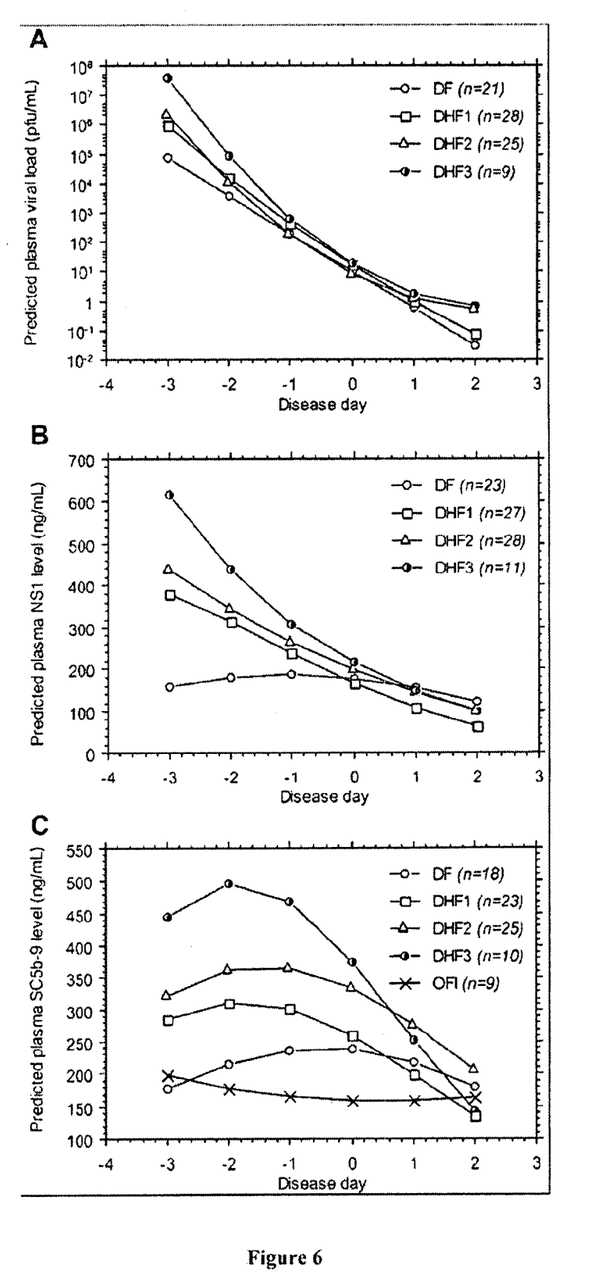
FIG. 6 illustrates predicted viral loads (A), NS1 levels (B), and SC5b-9 levels (C) from a mixed-model analysis. Dr, dengue fever; DHF, dengue hemorrhagic fever, OFI, other febrile illness.

DV RNA, NS1s, and complement activation products in clinical specimens. Measurements of DV RNA, NS1s, and SC5b-9 were performed in a blinded manner. FIG. 5 displays cross-sectional analysis of the mean and SD of each variable (viral load, NS1 level, and SC5b-9 level) over time, based on all available data. The highest viral loads were detected early during clinical illness in all patients and gradually declined to undetectable levels on day +1 in patients with DF or on day +2 in patients with DHF (FIG. 5A), in accordance with previous reports [9, 34]. The mean±SD level of NS1s in patients with DHF (383.9±620 ng/mL) was higher than that in patients with DF (181.6±120 ng/mL) during acute illness (FIG. 5B). NS1 was undetectable in patients with OFIs. Similarly, mean±SD plasma SC5b-9 levels were higher in patients with DHF (306.9±174 ng/mL) than in patients with DF (225.3±97 ng/ml) or OFIs (170.3±57 ng/mL) during acute illness (FIG. 5C). Because of missing viral load, NS1 level, and SC5b-9 level data at some time points, a mixed model of multivariate statistical analysis was applied. Only patients with at least 3 consecutive measurements were included in the analysis. This resulted in 83 patients and 301 observations for viral load, 89 patients and 319 observations for NS1 level, and 85 patients and 312 observations for SC5b-9 level. FIG. 6 displays plots of predicted viral load, NS1 level, and SC5b-9 level obtained from the quadratic mixed model against time. Viral load for patients with DF, DHF1, DHF2, or DHF3 decreased over time (FIG. 6A). There was a statistically significant difference in plasma viral load between patients with DF and some groups of patients with DHF (DF vs. DHF1, P=0.0856; DF vs. DHF2, P=0.0087; DF vs. DHF3, P=0.0599) and between patients with DF and all patients with DHF (P=0.0035). However, no difference in viral load was found among the different groups of patients with DHF (DHF1 vs. DHF2, P=0.1790; DHF1 vs. DHF3, P=0.3577; DHF2 vs. DHF3, P=0.4999).

NS1 levels significantly decreased over time in all groups of patients with DHF, whereas, in patients with DF, NS1 levels increased slightly during early acute illness, with a peak at day −1 or 0, and then gradually decreased (FIG. 6B). However, no statistically significant difference was observed among patients with the 3 types of DHF (DHF1 vs. DHF2, P=0.2811; DHF1 vs. DHF3, P=0.3158; DHF2 vs. DHF3, P=0.9123). The pattern of change in NS1 levels over time in patients with DF was significantly different from that in patients with DHF1 or DHF2 (DF vs. DHF1, P=0.0002; DF vs. DHF2, P=0.0042) but not patients with DHF3 (P=0.0761), which might have been due to the small sample size of this group. When all types of DHF were combined, a highly significant difference was found between patients with DF and patients with DHF (P<0.0001). Importantly, levels of NS1 during the febrile phase (days −3 to −1) could be used to differentiate between patients with DF and all groups of patients with DHF (day −3 and −2, P<0.0001; day −1, P=0.021). SC5b-9 levels exhibited a similar pattern in patients with DF and patients with DHF, reaching a peak at day −1 and day −2 for those with DF and those with DHF, respectively (FIG. 5C). No complement activation was round in patients with OFIS. Comparisons of SC5b-9 levels between patients with DF and all patients with DHF and between patients with DF and patients with OFIs revealed a statistical difference (P<0.0001). Levels of SC5b-9 observed during acute illness were highly correlated with disease severity−that is, the levels in patients with DHF3 were greater than those in patients with DHF2, and the levels in patients with DHF2 were greater than those in patients with DHF1 (DHF3 vs. DHF2. P=0.0052: DHF2 vs. DHF1, P=0.0507). Similar to NS1 levels, SC5b-9 levels in the febrile phase of DHF were significantly higher than those in patients with DF (day −3, P=0.0001; day −2, P<0.0001; day −1, P=0.0004).

Unlike NS1 levels, SC5b-9 levels could still be used to differentiate between DP and DHF at the day of defervescence (day 0, P=0.0183).

Example 6

NS1s and complement activation products in pleural fluids from patients with DSS. NS1, C3a and C5a, and SC5b-9 were measured in pleural fluids and ill plasma from 9 patients with DSS. Samples were collected at the day of shock or 1-2 days later. The results are shown in table 1. Pleural fluid levels of NS1 were similar to (patients 1-3) or higher than (patients 4-6) those in plasma. Pleural fluid levels of SC5b-9 were markedly higher than the plasma levels in all but 1 case. The mean±SD SC5b-9 level in pleural fluids was 2575.9±1121 ng/mL (range, 627-4865 ng/mL; median, 2312.5 ng/mL) and was significantly higher than the mean±SD level in plasma (1546.3±943 ng/mL; range, 394-2935 ng/mL; median, 1722 ng/mL) (P=0.04). A similar trend was found for C5a: the mean±SD level of this anaphylatoxin in pleural fluids was 47.4±61.1 ng/mL (range, 7-227 ng/mL; median, 23 ng/mL) and was also greater than that in plasma (25.6±33.9 ng/mL; range, 5-114 ng/mL; median, 15 ng/mL) (P=0.34). Results obtained for C3a were erratic, with no recognizable pattern (data not shown).

TABLE 1

Measurements of NS1, C5a, SC5b-9, and albumin in EDTA-treated plasma (P) and pleural fluid (PF) from 9 children with dengue shock syndrome.

| Patient | NS1 level, ng/ml | | C5a level, ng/ml | | SC5b-9 level, ng/ml | | Albumin level, g/L | |
|---|---|---|---|---|---|---|---|---|
| | P | PF | P | PF | P | PF | P | PF |
| 1 | 117 | 139 | 10 | 16 | 876 | 1369 | 13.6 | 12.9 |
| 2 | 120 | 122 | 20 | 17 | 2935 | 3516 | 26.7 | 19.5 |
| 3 | 2333 | 2058 | 10 | 21 | 1801 | 3353 | 3.3 | 2.5 |
| 4 | 116 | 337 | 5 | 7 | 691 | 627 | 9.8 | 9.6 |
| 5 | 141 | 3234 | 15 | 49 | 1722 | 2307 | 10.3 | 17.3 |
| 6 | 117 | 220 | 28 | 50 | 394 | 2764 | 29.5 | 20.6 |
| 7 | ND | ND | 19 | 14 | 1838 | 2270 | 13.4 | 3.7 |
| 8 | ND | ND | 9 | 20 | 750 | 1869 | 1 | 1.5 |
| 9 | ND | ND | 114 | 227 | 2910 | 4865 | 1.2 | 1.2 |

Figure 7:
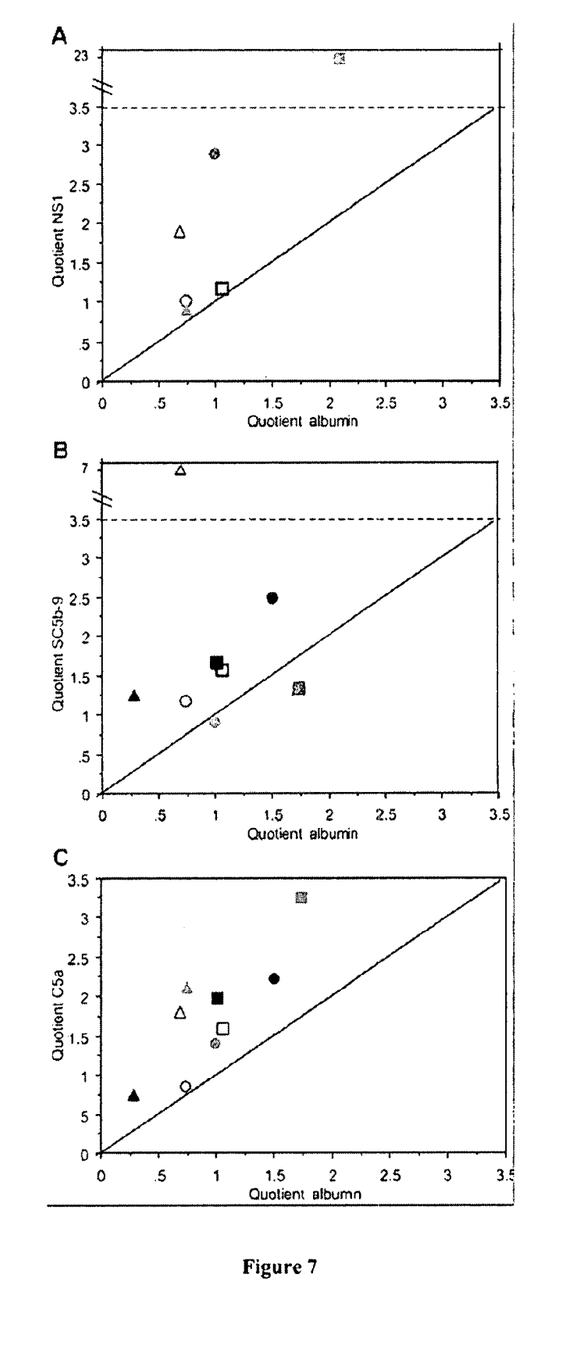
FIG. 7 illustrates Relative accumulation of NS1, SC5b-9, and C5a in pleural fluids. The quotients between pleural fluid and plasma levels of these analytes are plotted against the respective albumin quotients. Each symbol represents 1 patient.

When the pleural fluid-to-plasma ratios of NS1, SC5b-9, and C5a levels were plotted against the respective quotients for albumin, almost all plotted values came to lie above the diagonal. This indicated relative accumulation of the analytes, probably as a result of their local generation at the leakage site (FIG. 7).

All citations (e.g., scientific journal publications, patents, and other reference material) mentioned herein are hereby incorporated herein by reference to the same extent as if each individual citation was specifically and individually indicated to be incorporated by reference. In addition, examples described above are illustrative only and are not intended to limit the scope of the claims.

REFERENCES

1. Nimmannitya S. Clinical spectrum and management of dengue haemorrhagic fever. Southeast Asian J. Trop Med Public Health 1987; 18: 392-7.
2. Bhamarapravati N, Tuchinda P, Boonyapaknavik V. Pathology of Thailand haemorrhagic fever: a study of 100 autopsy cases. Ann Trop Med Parasitol 1967; 61:500-10.
3. Sangkawibha N, Rojanasuphot S, Ahandrik S, et al. Risk factors in dengue shock syndrome: a prospective epidemiologic study in Rayong, Thailand. I. The 1980 outbreak. Am J Epidemiol 1984; 120:653-69.
4. Guzman MG, Kouri G, Valdes L, et al. Epidemiologic studies on dengue in Santiago de Cuba, 1997. Am J Epidemiol 2000; 152:793-9.
5. Halstead S B, O'Rourke E J. Dengue viruses and mononuclear phagocytes. I. Infection enhancement by non-neutralizing antibody. J Exp Med 1977; 146:201-17.
6. Halstead S B. Pathogenesis of dengue: challenges to molecular biology. Science 1988; 239:470-81.
7. Mongkolsapaya J, Dejnirattisai W, Xu X N, et al. Original antigenic sin and apoptosis in the pathogenesis of dengue hemorrhagic fever. Nat Med 2003; 9:921-7.
8. Vaughn D W, Green S, Kalayanarooj S, et al. Dengue viremia titer, antibody response pattern, and virus serotype correlate with disease severity. J Infect Dis 2000; 181:2-9.
9. Murgue B, Roche C, Chungue E, Deparis X. Prospective study of the duration and magnitude of viraemia in children hospitalised during the 1996-1997 dengue-2 outbreak in French Polynesia. J Med Virol 2000; 60:432-8.
10. Libraty D H. Young P R, Pickering D, et al. High circulating levels of the dengue virus nonstructural protein NS1 early in dengue illness correlate with the development of dengue hemorrhagic fever. J Infect Dis 2002; 186:1165-8.
11. Bokisch V A, Top F H Jr, Russell P K, Dixon F J, Muller-Eberhard H J. The potential pathogenic role of complement in dengue hemorrhagic shock syndrome. N Engl J Med 1973: 289:996-1000.
12. Pathogenetic mechanisms in dengue haemorrhagic fever: report of an international collaborative study. Bull World Health Organ 1973; 48: 117-33.
13. Malasit P. Complement and dengue haemorrhagic fever/shock syndrome. Southeast Asian J Trop Med Public Health 1987; 18:316-20.
14. Bhakdi S, Kazatchkine M D. Pathogenesis of dengue: an alternative hypothesis. Southeast Asian J Trop Med Public Health 1990; 21:652-7.
15. Kurane I, Rothman A L. Livingston P G, et al. Immunopathologic mechanisms of dengue hemorrhagic fever and dengue shock syndrome. Arch Virol Suppl 1994; 9:59-64.
16. Halstead S B, Antibody, macrophages, dengue virus infection, shock, and hemorrhage: a pathogenetic cascade. Rev Infect Dis 1989; 11 (Suppl 4):S830-9.
17. Avirutnan P. Malasit P, Seliger B, Bhakdi S, Husmann M. Dengue virus infection of human endothelial cells leads to chemokine production, complement activation, and apoptosis. J Immunol 1998; 161:6338-46.
18. Winkler (, Maxwell S E, Ruemminer C, Stollar V. Newly synthesized dengue-2 virus nonstructural protein NS1 is a soluble protein but becomes partially hydrophobic and membrane-associated alter dimerization. Virology 1989; 171:302-5.
19. Flamand M, Megret F, Mathieu M, Lepault J, Rey F A, Deubel V. Dengue virus type 1 nonstructural glycoprotein NS1 is secreted from mammalian cells as a soluble hexamer in a glycosylation-dependent fashion. J Virol 1999; 73:6104-10.
20. Schlesinger J J, Brandriss M W. Walsh E E. Protection of mice against dengue 2 virus encephalitis by immunization with the dengue 2 virus non-structural glycoprotein NS1. J Gen Virol 1987; 68:853-7.
21. Henchal E A, Henchal L S, Schlesinger J J. Synergistic interactions of anti-NS1 monoclonal antibodies protect passively immunized mice from lethal challenge with dengue 2 virus. J Gen Virol 1988; 69:2101-7.
22. Falgout B, Bray M, Schlesinger J J, Lai C J. Immunization of mice with recombinant vaccinia virus expressing authentic dengue virus nonstructural protein NS1 protects against lethal dengue virus encephalitis. J Virol 1990; 64:4356-63.

23. Qu X, Chen W V Maguire T, Austin F. Immunoreactivity and protective effects in mice of a recombinant dengue 2 Tonga virus NS1 protein produced in a baculovirus expression system. J Gen Virol 1993; 74:89-97.

24. Young P R, Hilditch P A, Bletchly C, Halloran W. An antigen capture enzyme-linked immunosorbent assay reveals high levels of the dengue virus protein NS1 in the sera of infected patients. J Clin Microbiol 2000; 38:1053-7.

25. Alcon S, Talarmin A, Debruyne M, Falconar A, Deubel V, Flamand M. Enzyme-linked immunosorbent assay specific to dengue virus type 1 nonstructural protein NS1 reveals circulation of the antigen in the blood during the acute phase of disease in patients experiencing primary or secondary infections. J Clin Microbiol 2002; 40:370-81.

26. Hugli T, Muller-Eberhard H J. Anaphylatoxins: C3a and C5a. Adv Immunol 1978; 26:1-55.

27. Bossi F. Fischetti F, Pellis V, et al. Platelet-activating factor and kinindependent vascular leakage as a novel functional activity of the soluble terminal complement complex. J Immunol 2004; 173:6921-7.

28. Ishikawa S. Tsukada H, Bhattacharya J. Soluble complex of complement increases hydraulic conductivity in single microvessels of rat lungs. J Clin Invest 1993; 91:103-9.

29. Puttikhunt C, Kasinrerk W, Srisa-ad S, et al. Production of anti-dengue NS1 monoclonal antibodies by DNA immunization. J Virol Methods 2003; 109:55-61.

30. Sambrook J, Russell D W. Introducing cloned genes into cultured mammalian cells: calcium-phosphate-mediated transfection of eukaryotic cells with plasmid DNAs. 3th ed. New York: Cold Spring Harbor Laboratory Press, Cold Spring Harbor, 2001.

31. Shu P Y, Chang S F, Kuo Y C, et al. Development of group- and serotypespecific one-step SYBR green 1-based real-time reverse transcription-PCR assay for dengue virus. J Clin Microbiol 2003; 41:2408-16.

32. Yenchitsomanus P T, Sricharoen P, Jaruthasana J, et al. Rapid detection and identification of dengue viruses by polymerase chain reaction (PCR). Southeast Asian J Trop Med Public Health 1996; 27:228-36.

33. Dengue haemorrhagic fever: diagnosis, treatment, prevention and control. Geneva: World Health Organization, 1997.

34. Sudiro T M, Zivny J, Ishiko H, et al. Analysis of plasma viral RNA levels during acute dengue virus infection using quantitative competitor reverse transcription-polymerase chain reaction. J Med Virol 2001; 63: 29-34.

35. Morgan B P. Regulation of the complement membrane attack pathway. Crit Rev Immunol 1999; 19:173-98.

36. Tedesco F, Pausa M, Nardon E, Introna M, Mantovani A, Dobrina A. The cytolytically inactive terminal complement complex activates endothelial cells to express adhesion molecules and tissue factor procoagulant activity. J Exp Med 1997; 185:1619-27.

37. Dobrina A. Pausa M, Fischetti F, et al. Cytolytically inactive terminal complement complex causes transendothelial migration of polymorphonuclear leukocytes in vitro and in vivo. Blood 2002; 99:185-92.

38. Casarsa C, De Luigi A, Pausa M, De Simoni M G, Tedesco F. Intracerebroventricular injection of the terminal complement complex causes inflammatory reaction in the rat brain. Eur J Immunol 2003; 33:1260-70.

39. Jessie K, Fong M Y, Devi S, Lam S K, Wong K T. Localization of dengue virus in naturally infected human tissues, by immunohistochemistry and in situ hybridization. J Infect Dis 2004: 189:1411-8.

40. Hugo F, Berstecher C, Kramer S, Fassbender W, Bhakdi S. In vivo clearance studies of the terminal fluid-phase complement complex in rabbits. Clin Exp Immunol 1989; 77:112-6.

41. Greenstein J D, Peake P W, Charlesworth J A. The kinetics and distribution of C9 and SC5b-9 in vivo: effects of complement activation. Clin Exp Immunol 1995; 100:40-6.

42. Brandt W E, Chiewslip D, Harris D L, Russell P K. Partial purification and characterization of a dengue virus soluble complement-fixing antigen. J Immunol 1970; 105:1565-8.

43. McCloud T G. Brandt W E, Russell P K. Molecular size and charge relationships of the soluble complement-fixing antigens of dengue viruses. Virology 1970; 41:569-72.

What is claimed is:

1. A method of determining risk of developing Dengue Hemorrhagic Fever/Dengue Shock Syndrome (DHF/DSS) in an individual infected with dengue virus (DV), the method comprising:

determining, in a fluid or tissue sample of the individual, the presence, absence or quantity of dengue virus protein NS1; and determining, in a fluid or tissue sample of the individual, presence, absence or quantity of SC5b-9 complement complex wherein the individual is at risk of developing DHF/DSS if a) the amount of NS1 protein is at least 90 ng/mL and b) the amount of SC5b-9 complement complex is at least 200 ng/mL.

2. A method in accordance with claim 1, wherein determining presence, absence or quantity of dengue virus protein NS1 comprises:

a) contacting a fluid or tissue sample from an individual with a solid surface comprising a first probe which specifically binds NS1 protein, wherein a complex forms comprising the first probe and the NS1 protein, if present in the sample;

b) contacting the solid surface with a second probe which specifically binds NS1 protein; and c) determining quantity of the second probe bound to the surface.

3. A method in accordance with claim 2, wherein the first probe and the second probe are each independently selected from the group consisting of an antibody, an aptamer, a kinase, an avimer and a combination thereof.

4. A method in accordance with claim 2, wherein each probe is an antibody independently selected from the group consisting of a polyclonal antibody and a monoclonal antibody.

5. A method in accordance with claim 1, wherein determining presence, absence or quantity of SC5b-9 complement complex comprises:

a) contacting a fluid or tissue sample from the individual with a solid surface comprising a first probe which specifically binds SC5b-9 complement complex, wherein a complex forms comprising the first probe and the SC5b-9 complement complex, if present in the sample;

b) contacting the solid surface with a second probe which specifically binds SC5b-9 complement complex; and c) determining quantity of the second probe bound to the surface.

6. A method in accordance with claim 5, wherein the first probe and the second probe are each independently selected from the group consisting of an antibody, an aptamer, a kinase, an avimer and a combination thereof.

7. A method in accordance with claim 5, wherein each probe is an antibody independently selected from the group consisting of a polyclonal antibody and a monoclonal antibody.

8. A method in accordance with claim 1, wherein the fluid or tissue sample is a body fluid sample selected from the group consisting of a blood sample, a serum sample, a plasma sample, a lymphatic fluid sample and a cerebrospinal fluid sample.

9. A method in accordance with claim 1, wherein the determining risk further comprises: comparing the quantity of dengue virus protein NS1 and the quantity of SC5b-9 complement complex to a database comprising epidemiological statistics correlating quantity of dengue virus protein NS1 and quantity of SC5b-9 complement complex with the probability of developing DHF/DSS.

* * * * *